(12) United States Patent
Parnell

(10) Patent No.: US 10,492,543 B2
(45) Date of Patent: Dec. 3, 2019

(54) HEATED SOCK TO KEEP THE WEARER FEET AND TOES WARM

(71) Applicant: Tevian Parnell, Big Spring, TX (US)

(72) Inventor: Tevian Parnell, Big Spring, TX (US)

( * ) Notice: Subject to any disclaimer, the term of this patent is extended or adjusted under 35 U.S.C. 154(b) by 214 days.

(21) Appl. No.: 15/879,496

(22) Filed: Jan. 25, 2018

(65) Prior Publication Data

US 2018/0146718 A1    May 31, 2018

Related U.S. Application Data

(63) Continuation-in-part of application No. 15/046,360, filed on Feb. 17, 2016, now abandoned.

(51) Int. Cl.
| | |
|---|---|
| *A41B 11/00* | (2006.01) |
| *A61F 7/03* | (2006.01) |
| *A61F 7/02* | (2006.01) |
| *A61F 7/00* | (2006.01) |
| *A41D 13/002* | (2006.01) |
| *A41D 13/06* | (2006.01) |

(52) U.S. Cl.
CPC .......... *A41B 11/004* (2013.01); *A41B 11/006* (2013.01); *A61F 7/032* (2013.01); *A61F 7/034* (2013.01); *A41B 2400/60* (2013.01); *A41B 2500/10* (2013.01); *A41B 2500/50* (2013.01); *A41D 13/002* (2013.01); *A41D 13/06* (2013.01); *A61F 2007/0044* (2013.01); *A61F 2007/0045* (2013.01); *A61F 2007/0233* (2013.01); *A61F 2007/0238* (2013.01); *A61F 2007/0266* (2013.01)

(58) Field of Classification Search
CPC .. A41B 11/006; A41D 13/06; A41D 13/0543; A61F 7/0241; A61F 7/03
USPC .......................................................... 2/239
See application file for complete search history.

(56) References Cited

U.S. PATENT DOCUMENTS 6,576,003 B2 *   6/2003   Kotack ................... A43B 1/10
                                                36/2.6

\* cited by examiner

*Primary Examiner* — Timothy K Trieu
(74) *Attorney, Agent, or Firm* — Bruce A. Lev

(57) ABSTRACT

Heated socks used to keep a wearer's feet and toes warm. The heated socks include pockets for oxygen-activated chemical heating pouches which generate heat when exposed to air and via friction caused by the wearer when walking, jumping, or other activities and distributed through the sock from toe to ankle to heel. The heated socks are provided with extra cushioning on the bottom of the feet to aid in comfort for the wearer. The heated socks also keep the feet dry from moisture and perspiration.

19 Claims, 3 Drawing Sheets

HEATED SOCK TO KEEP THE WEARER FEET AND TOES WARM

CROSS-REFERENCE TO RELATED APPLICATION

The present application is related to and claims priority from prior Non-Provisional patent application Ser. No. 15/046,360, filed Feb. 17, 2016 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates to a heated garment system, and more particularly, to 15 heated socks with a pocket for receiving a pervious oxygen-activated chemical heating pouch to keep the wearer's feet and toes warm.

2. Description of the Related Art

Cold weather and winter sports are very popular. Hunting, fishing, walking, hiking, game-watching and camping are often at their best in cooler weather. In addition, athletic sports such 20 as football, soccer, skiing and ice skating are done during the winter. These and other winter activities require protection from the cold with proper clothing to best enjoy the sport. For a spectator, or an active participant, the feet and hands are most vulnerable to the cold. There have been many devices suggested to provide needed warmth to these areas including passive devices which provide additional insulation to hold the body's own heat and active devices which generate heat and apply the heat to the needed areas of the body. Also, many people suffer from foot pain and discomfort, which may be due to various factors that may include injury, structural imbalance and excessive activity. These factors lead to various foot conditions such as plantar fascitis, metatarsalgia, bunions, heel 5 pain, as well as blisters, corns and calluses. Various attempts to alleviate foot pain and discomfort have been developed including the use of cushioned hosiery, such as stockings and socks.

U.S. Pat. No. 4,705,935, issued Nov. 10, 1987, to Albert Traffanstedt and Roy Traffanstedt, discloses a pair of heatable socks for keeping the wearer's feet warm in a cold 10 environment and comprising a resistive heating unit secured in the toe of each sock, a battery source which is carried on the wearer's body, and switching means controllable by the wearer for acting in combination with the resistive heating unit to selectively cause different and controllable amounts of electric current from the battery source to flow through the resistive heating units to thereby generate different and desired amounts of heat in the socks.

Other U.S. Pat. No. 3,906,185 to Gross and U.S. Pat. No. 2,692,326 to Crowell show a shoe heated by a resistive element which is powered by a battery carried on the wearer's clothes. Both of these also disclose battery powered resistive elements in which the maximum battery voltage is always connected across the entire resistive heating element and, accordingly, will usually heat the heating elements to a higher than needed and perhaps uncomfortable temperature when the battery is fresh and fully charged and then, after an hour or two, when the user is tried and the cold has penetrated well into the shoes, the battery will be partially discharged and will not be able to heat the resistive heating elements to a foot comfortable temperature.

U.S. Pat. No. 5,230,333, issued Jul. 27, 1993, provides "Thermal sock having a toe 25 heating pocket". This was developed to provide an improved thermal sock construction for warming the toes of the user by means of a chemical heating pouch inserted into a pocket formed on the top of the toe portion of the sock.

Accordingly, a need remains for a warming or heating apparatus for keeping the feet warm and the like. As such, it may be appreciated that there continues to be a need for a new and improved heated socks as set forth by the instant invention which addresses the problems of ease of use as well as effectiveness in construction in providing the heated socks for 5 use in providing warmness and aids in comfort to the feet of the user and in this respect, the present invention substantially fulfills this need.

BRIEF SUMMARY OF THE INVENTION

In view of the foregoing disadvantages inherent in the known types of feet and toes warming apparatus now present in the prior art, the present invention provides the heated socks wherein the same utilizes an oxygen-activated heating chemical for warming the feet of the user and use on process of various components employed in the procedure. As such, the general purpose of the present invention, which will be described subsequently in greater detail, is to provide new and improved heated socks which has all the advantages of the prior art and none of the disadvantages.

Accordingly, it is a primary aspect of the present invention to provide the heated socks, which keeps the wearer's feet and toes warm. For the purpose, heat is caused by the chemical exposed to air. In another aspect, the present invention provides the heated socks which comprise a pocket for oxygen-activated chemical heating pouch. In another aspect, the present invention provides the heated socks which cause heat through friction. It is yet another aspect of the present invention where the heated socks are provided with the extra cushion on the bottom of the feet to aid in comfort for the person.

Further aspect of the present invention provides the heated socks which have been shaped to fit within footwear to provide warmth and comfort to the feet of the wearer. It is still another aspect of the present invention to provide new and improved heated socks which may be easily and efficiently manufactured and marketed. It is a further aspect of the present invention to provide new and improved heated socks which is of a durable and reliable construction.

An even further aspect of the present invention is to provide new and improved heated socks which is susceptible to a low cost of manufacture with regard to both materials and labor, and which accordingly is then susceptible of low prices of sale to the consuming public, thereby making such heated socks economically available to the buying public.

Other aspects of the present invention will become apparent from time to time throughout the specification as hereinafter related. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

These together with other objects of the invention, along with the various features of novelty which characterize the invention, are pointed out with particularity in the disclosure. For a better understanding of the invention, its operating advantages and the specific objects attained by its uses, reference should be had to the accompanying drawings and descriptive matter in which there are illustrated preferred embodiments of the invention.

The present invention holds significant improvements and serves a Heated Sock To Keep The Wearer Feet And Toes Warm. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, a Heated Sock To Keep The Wearer Feet And Toes Warm, constructed and operative according to the teachings of the present invention.

The various embodiments of the present invention will hereinafter be described in conjunction with the appended drawings, wherein like designations denote like elements.

DETAILED DESCRIPTION

Various aspects of the illustrative embodiments will be described using the terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

In some preferred embodiments, the present invention provides the heated socks which allow the wearer to always have warm feet and toes. The heating element is inbuilt in the heated socks, provided with the pocket, which comprises the oxygen activated heating chemical pouch. The heating chemical generates heat as it is exposed to the air. Further, when the wearer causes friction by running or jumping or even walking, the heat generates and extends from top of the toe to the heel portion.

The inventive product provides comfort to the wearer as the cushion element is provided within the sock. Also, the inventive product would prove to be beneficial to keep the feet dry for longer hours. Moreover, if the foot perspires, the moisture does 5 not affect the heating capability of the warmer.

Figure 2:
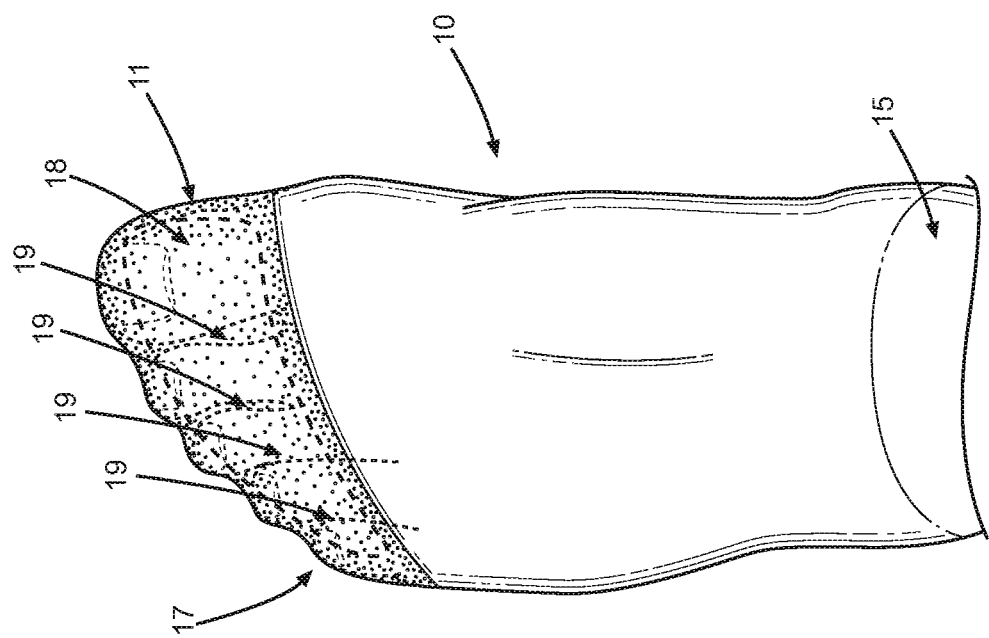
FIG. 2 shows a top view illustrating the user's foot wearing the heated socks according to an embodiment of the present invention.
Figure 1:
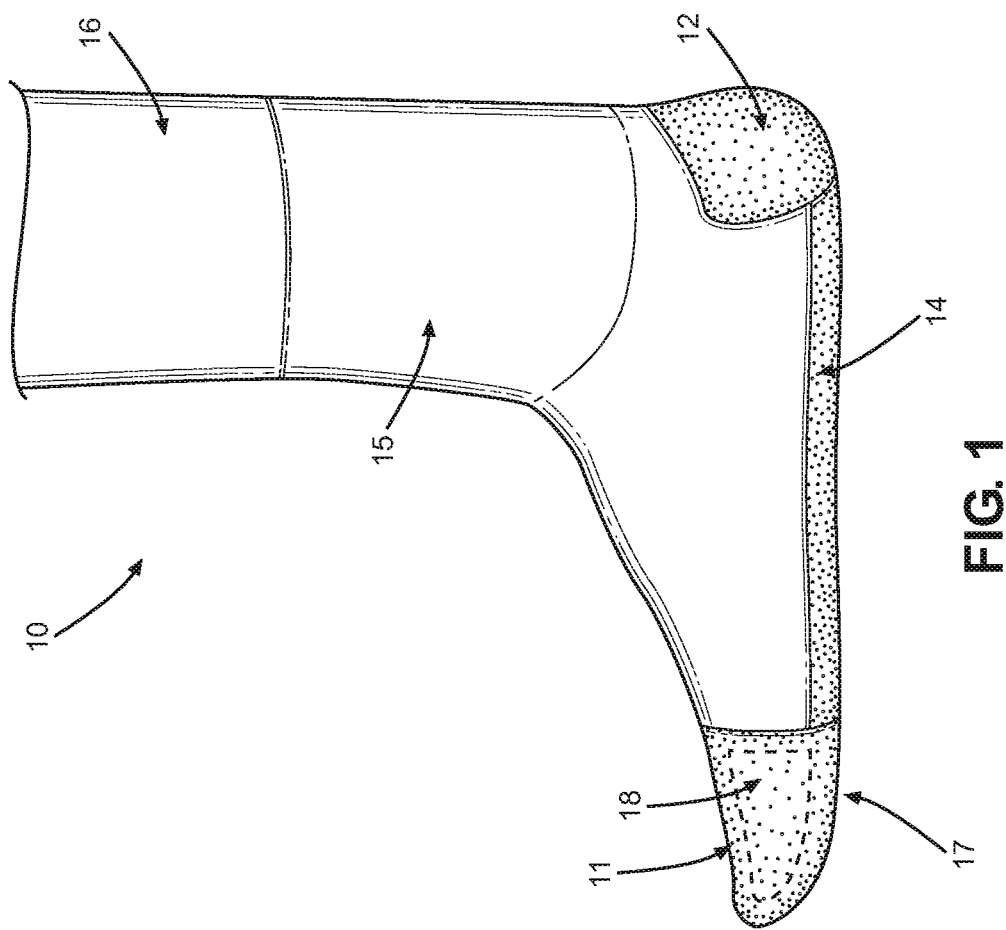
FIG. 1 shows a side view illustrating a user's foot wearing the heated socks according to an embodiment of the present invention.
Figure 3:
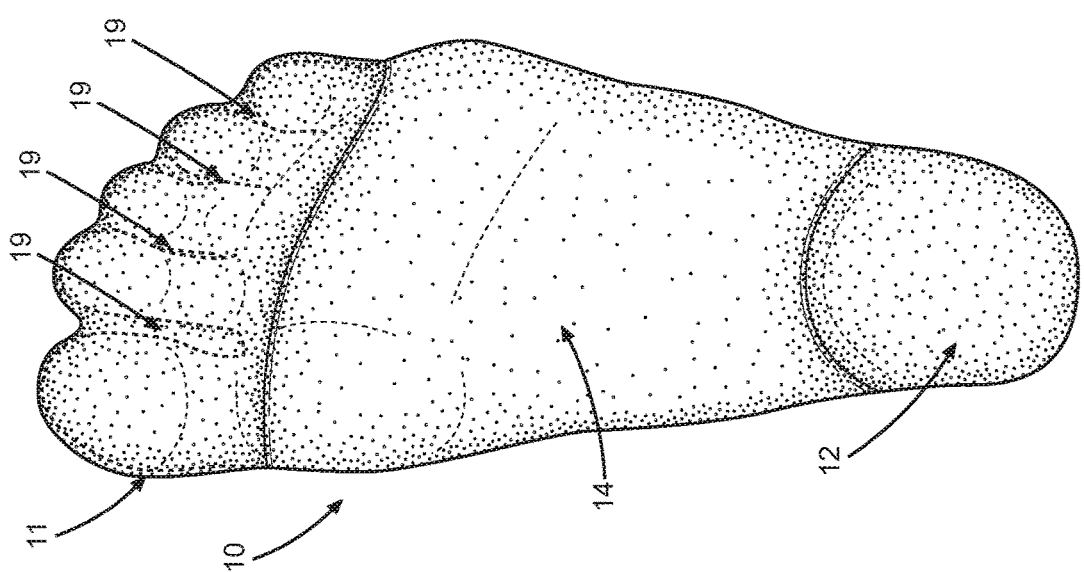
FIG. 3 shows a bottom view illustrating a heated sock according to an embodiment of the present invention.

With reference now to the drawings, and in particular to FIGS. 1-3 thereof, new and improved heated socks embodying the principles and concepts of the present invention are described herein. An embodiment of the heated sock apparatus according to this invention is designated generally by the reference character 10.

FIGS. 1-3, the side view of the heated sock 10 includes a toe portion 11 having slat members 19, a heel portion 12, a sole portion 14, an ankle portion 15, and an elastic ribbed calf portion 16. The sock comprises a pocket structure 17 to enclose the oxygen-activated chemical heating pouch 18. The chemical heating pouch 18 as exposed to air tends to generate the heat. The heat is also caused by the friction created by the wearer. The heat travels from the toe portion 11 to the heel portion 12 and ankle portion 15; spreads in the whole foot both upper and bottom side of the foot.

Further FIG. 2 and FIG. 3 illustrates the top and bottom view respectively, of the heated sock 10 enclosing one or more components as discussed above.

The heated sock of the present invention is formed of a relatively thick knitted fabric material—such as wool, a synthetic fiber/wool or cotton-polypropylene blend, or the like—as normally used in socks. Preferably, the heated sock is formed of Marino wool with at least one or more in combination from the three materials: HOLLOFIL, THERMAX, or THERMOSTAT. In accordance with the invention, the heated sock also comprises the synthetic wicking material like polypropylene and COOLMAX woven into the sock to enhance the moisture wicking performance of the heated sock.

Another embodiment discloses the cushion element provided in the sock comprises the material like acrylic weaved into one or more area(s) to increase the density of the cushion, especially in the areas which causes stress to the foot while walking or hiking or the like activities, and thereby which aids in providing comfort to the wearer. Further, the heated sock also comprises supporting materials like stretch nylon or spandex to facilitate the shape of the sock and to minimize the wrinkles of the fabric.

The sock design can be made as no-show, ankle, or crew socks. Each sock can have different areas having the heat chemicals. Some designated areas for the heat chemicals can be the toes, the heel, the bottom of foot, and the top of foot. The chemicals will be dispersed in a way that the wearer can wear the sock comfortably without the heated areas feeling bulky. Particular details of each of these areas are as follows:

Toes: The material for designated heat area will begin at the top of the toes, go around the front of the toes, and continue down around the bottom of the toes. There will be a seam around that area connecting it to the rest of the sock (like a regular sock's seam would appear but this would have the heating chemicals inside total area).

Top of foot: This area will have a rectangular or square shaped seam/hem with the heat chemicals sewn inside.

Bottom of foot: This area will span the bottom of the foot from under the ball of the foot to right before the heel area. The seams will also slightly come up and around the inner and outer edges of the foot. The heating chemical will be sewn into this area.

Heel: This area's seams will cup itself around the heel, and slightly go up the back of the foot (for shorter socks) or up the back of the foot higher ending toward the back ankle area (for longer socks). The socks can be made with a thicker weave for added cushion.

Figure 4:
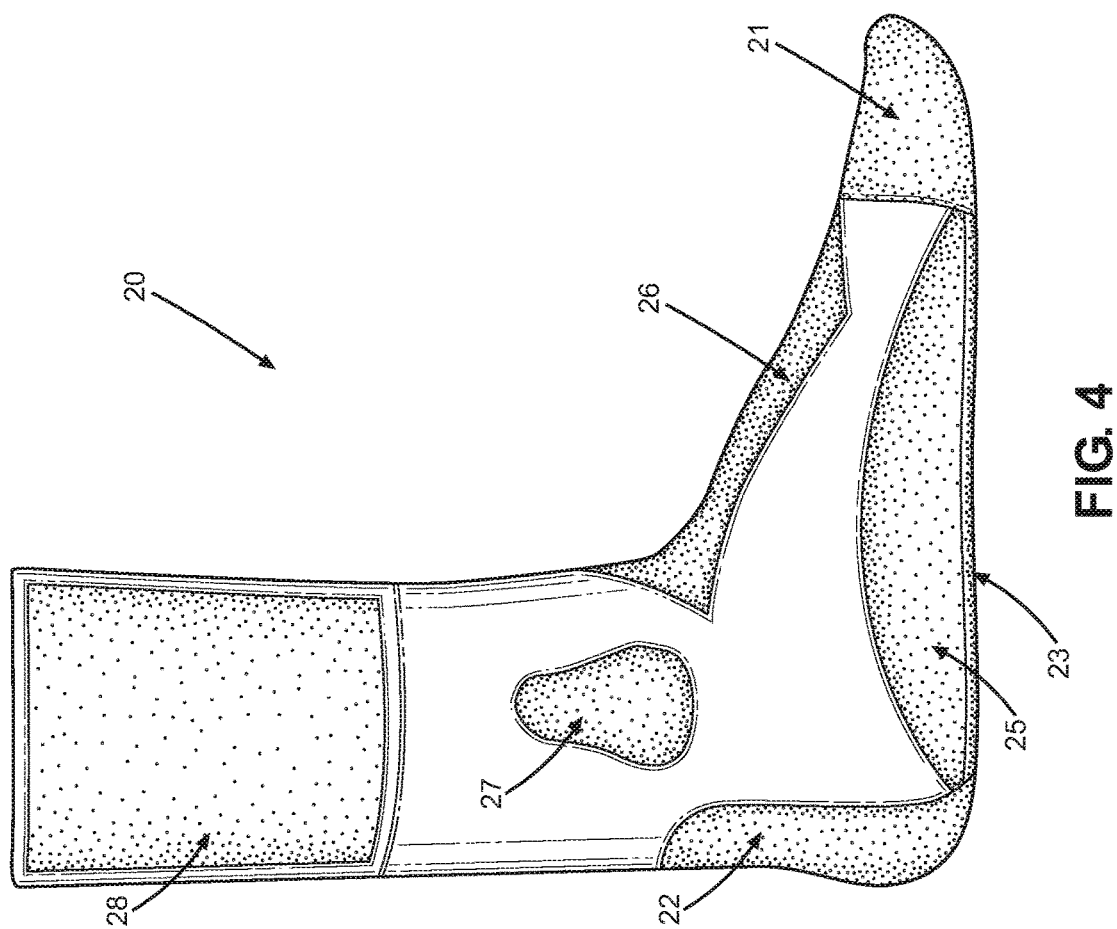
FIG. 4 shows an outer side view illustrating the heated socks according to the preferred embodiment of the present invention.
Figure 6:
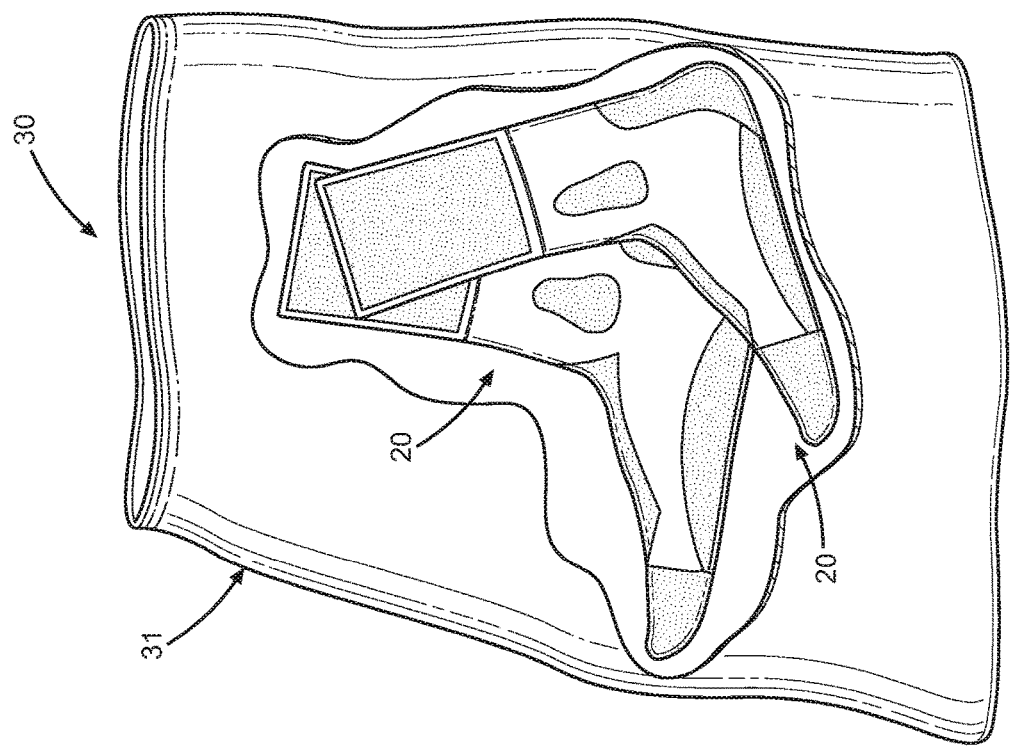
FIG. 6 shows a perspective view illustrating a combination of a pair of heated socks for warming a wearer's foot and an air-tight packaging member of the preferred embodiment of the present invention.
Figure 5:
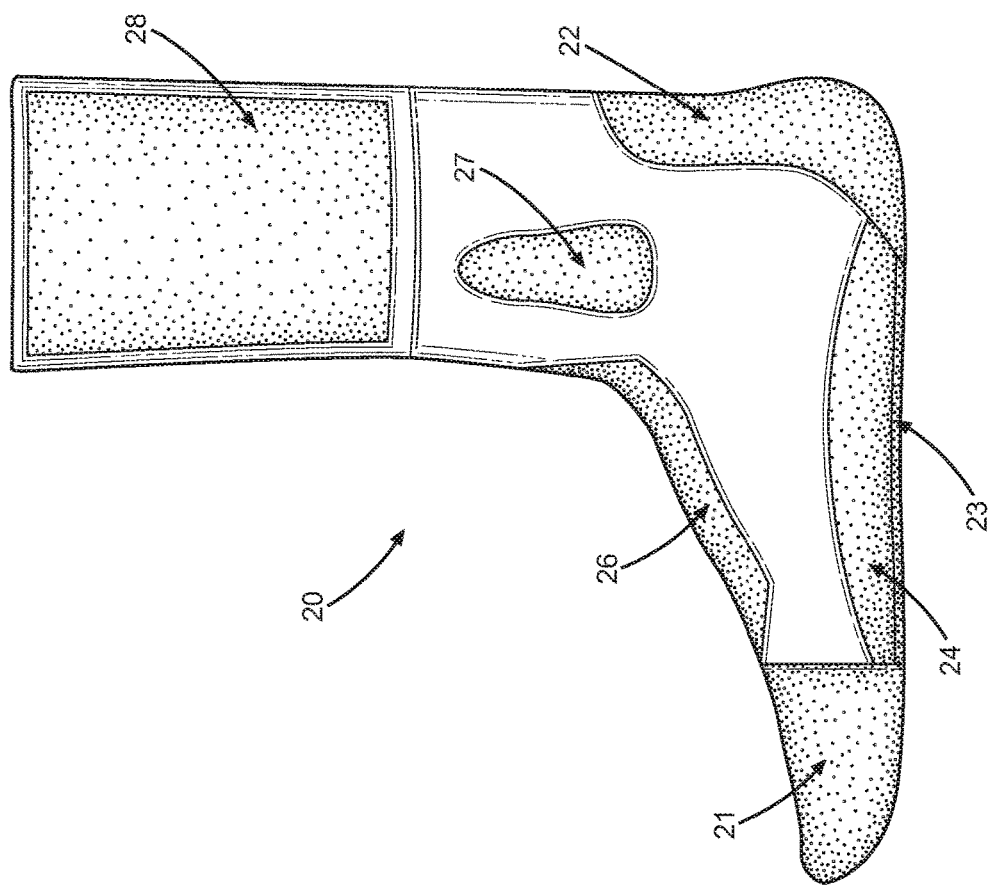
FIG. 5 shows an inner side view illustrating the heated socks according to the preferred embodiment of the present invention.

Referring now to the preferred embodiment of the invention illustrated in FIGS. 4-6, heated socks 20 for warming a wearer's foot comprises a sock body including a toe portion 21, a heel portion 22, a sole portion 23, an inner edge portion 24, an outer edge portion 25, an upper portion 26 at least one ankle portion 27, and an upper ankle portion 28; a plurality of pocket members 17 respectively attached to the toe portion, the heel portion, the sole portion, the inner edge portion, the outer edge portion, the at least one ankle portion, and the upper ankle portion; and a plurality of heating pouch members 18, each including a pouch body including an exterior surface and an interior volume, and wherein the pouch body is formed from a pervious, flexible material, and an oxygen activated chemical removably located within the interior volume and adapted to create and dissipate heat when exposed to and combined with oxygen; and wherein the plurality of heating pouch members are respectively placed within respective plurality of pocket members, such that the foot of said wearer can be warmed by the heated sock.

Further features of the preferred embodiment include the oxygen activated chemical being adapted and configured to generate heat via chemical reaction with oxygen or via friction between a wearer's foot and the heated sock when in use. The sock body may also include a cushioning element for providing comfort to the wearer, and wherein the cushioning element may be formed from a knitted fabric material including wool, synthetic fibers, synthetic wool, or a cotton-polypropylene blend. The knitted fabric wool can be formed from MERINO wool combined with a polyester material, or in combination with HOOLOFIL, THERMA, and THERMOSTAT materials. The sock body may also be formed from a material that includes a synthetic wicking material, and wherein the synthetic wicking material may be polypropylene or COOLMAX to enhance the moisture wicking performance of the heated sock. The sock body may also be formed from a material including stretchable nylon to facilitate the shape of the sock body and to minimize wrinkles in the sock body, and wherein the stretchable nylon material may be SPANDEX.

As per the positioning of the sock body portions, the inner and outer edge portions can be attached to respective opposite sides of the sole portion, the toe portion can be attached to a front edge of the sole portion, the heel portion can be attached to a back edge of the sole portion, the toe portion can be attached to a front edge of the sole portion, and the top portion can be attached to a top edge of the toe portion.

As a further feature of the preferred embodiment, the toe portion may include a plurality of slat members 19 each adapted to reside between and warm two adjacent toes of a foot of a wearer. As such, there may be four slat members in the toe portion to respectively reside between five toes of a foot of the wearer.

Further details of the preferred embodiment includes the oxygen activated chemicals including iron powder, activated charcoal, sodium chloride, and vermiculite. Particular functions of each of these chemicals are as follows:

Iron powder: Oxygen in the air reacts with this powder to create iron oxide—rust and heat—usually heating to 163 degrees Fahrenheit.

Activated charcoal: This is a porous material that holds water—this is necessary for the oxidizing reaction to take place. It is thermally conductive, so it helps evenly spread heat.

Sodium chloride: catalyst in the process to help kick start the rust reaction.

Vermiculite: A hydrated magnesium aluminum silicate—it expands when heated and is a light, highly absorbent, odorless, chemically inert, fire resistant material. It is a great insulator. Along with the activated charcoal, it helps diffuse iron powder so the filling doesn't burn too quickly resulting in injury burns to wearer.

As illustrated in FIG. 6, the socks can be packaged in a way that no oxygen is in contact with the socks before use since oxygen is what activates the chemicals to heat the socks. As such, a combination 30 of a pair of heated socks 20 for warming a wearer's feet and an air-tight packaging member 31 is set forth, wherein the air-tight packaging member includes a main body adapted to retain a pair of the heated socks in an air-free environment therein; and wherein the pair of heated socks are placed within and stored within the air-tight packaging member until the air-tight packaging member is opened, the pair of heated socks are removed, and the pair of heated socks are ready to be worn.

It should be noted that the steps described in the method of use can be carried out in many different orders according to user preference. The use of "step of" should not be interpreted as "step for", in the claims herein and is not intended to invoke the provisions of 35 U.S.C. § 112, ¶6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed:

1. A heated sock for warming a wearer's foot, comprising:
a sock body including:
   a toe portion;
   a heel portion;
   a sole portion;
   an inner edge portion;
   an outer edge portion;
   an upper portion;
   at least one ankle portion; and
   an upper ankle portion;
a plurality of pocket members;
   wherein said plurality of pocket members are respectively attached to said toe portion, said heel portion, said sole portion, said inner edge portion, said outer edge portion, said upper portion, said at least one ankle portion, and said upper ankle portion; and
a plurality of heating pouch members, each of the pouch members including:
   a pouch body including:
      an exterior surface; and
      an interior volume; and
      wherein said pouch body is formed from a pervious, flexible material; and
   an oxygen activated chemical;
      wherein said oxygen activated chemical is removably located within said interior volume;
      wherein said oxygen activated chemical is adapted to create and dissipate heat when exposed to and combined with oxygen;
   wherein said plurality of heating pouch members are respectively placed within respective said plurality of pocket members, such that said foot of said wearer can be warmed by said heated sock.

2. The heated sock as claimed in claim 1, wherein said oxygen activated chemical is also adapted and configured to generate heat via friction between a wearer's foot and said heated sock.

3. The heated sock as claimed in claim 1, wherein said sock body includes a cushioning element for providing comfort to the wearer.

4. The heated sock as claimed in claim 3, wherein said cushioning element is formed from a knitted fabric material.

5. The heated sock as claimed in claim 4, wherein said knitted fabric material is chosen from a group of knitted fabric materials consisting of wool, synthetic fibers, synthetic wool, and a cotton-polypropylene blend.

6. The heated sock as claimed in claim 5, wherein said knitted fabric wool merino wool combined with a polyester material.

7. The heated sock as claimed in claim 6, wherein said knitted fabric wool is formed in combination with a material chosen from a group of materials consisting of hoolofil, therma, and thermostat.

8. The heated sock as claimed in claim 1, wherein said sock body is formed from a material including a synthetic wicking material.

9. The heated sock as claimed in claim 1, wherein said synthetic wicking material is chosen from a group of synthetic wicking materials consisting of polypropylene and coolmax to enhance the moisture wicking performance of the heated sock.

10. The heated sock as claimed in claim 1, wherein said sock body is formed from a material including stretchable nylon to facilitate the shape of the sock body and to minimize wrinkles in the sock body.

11. The heated sock as claimed in claim 1, wherein said sock body is formed from a material including spandex to facilitate the shape of the sock body and to minimize wrinkles in the sock body.

12. The heated sock as claimed in claim 1, wherein said inner and outer edge portions are attached to respective opposite sides of said sole portion.

13. The heated sock as claimed in claim 12, wherein said toe portion is attached to a front edge of said sole portion.

14. The heated sock as claimed in claim 13, wherein said heel portion is attached to a back edge of said sole portion.

15. The heated sock as claimed in claim 14, wherein said toe portion is attached to a front edge of said sole portion.

16. The heated sock as claimed in claim 15, wherein said top portion is attached to a top edge of said toe portion.

17. The heated sock as claimed in claim 1, wherein said toe portion includes a plurality of slat members each adapted to reside between and warm two adjacent toes of a foot of said wearer.

18. The heated sock as claimed in claim 1, wherein there are four slat members in said toe portion and adapted to respectively reside between five toes of a foot of said wearer.

19. A combination of a pair of heated socks for warming a wearer's feet and an air-tight packaging member, wherein said combination comprising: said air-tight packaging member including:
   a main body; wherein said main body is adapted to retain said pair of heated socks in an air-free environment therein; and said pair of heated socks, each of said pair of heated socks including: a sock body including: a toe portion; a heel portion; a sole portion; an inner edge portion; an outer edge portion; an upper portion; at least one ankle portion; and an upper ankle portion; a plurality of pocket members;
   wherein said plurality of pocket members are respectively attached to said toe portion, said heel portion, said sole portion, said inner edge portion, said outer edge portion, said upper portion, said at least one ankle portion, and said upper ankle portion; and a plurality of heating pouch members, each including: a pouch body including: an exterior surface; and an interior volume; and
   wherein said pouch body is formed from a pervious, flexible material; and an oxygen activated chemical;
   wherein said oxygen activated chemical is removably located within said interior volume;
   wherein said oxygen activated chemical is adapted to create and dissipate heat when exposed to and combined with oxygen;
   wherein said plurality of heating pouch members are respectively placed within respective said plurality of pocket members, such that said foot of said wearer can be warmed by said heated sock; wherein said pair of heated socks are placed within and stored within said air-tight packaging member until said air-tight packaging member is opened, said pair of heated socks are removed, and said pair of heated socks are ready to be worn.

* * * * *